United States Patent
Iwase et al.

(10) Patent No.: US 8,734,390 B2
(45) Date of Patent: May 27, 2014

(54) INJECTION AID AND MEDICATION SYRINGE DEVICE

(75) Inventors: Yoichiro Iwase, Ashigarakami-gun (JP); Takayuki Yokota, Nakakoma-gun (JP); Yoshinori Hishikawa, Nakakoma-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 56 days.

(21) Appl. No.: 13/497,712

(22) PCT Filed: Sep. 6, 2010

(86) PCT No.: PCT/JP2010/065247
§ 371 (c)(1),
(2), (4) Date: Mar. 22, 2012

(87) PCT Pub. No.: WO2011/040188
PCT Pub. Date: Apr. 7, 2011

(65) Prior Publication Data
US 2012/0191042 A1 Jul. 26, 2012

(30) Foreign Application Priority Data
Sep. 30, 2009 (JP) ................................. 2009-228549

(51) Int. Cl.
*A61M 5/00* (2006.01)
(52) U.S. Cl.
USPC ....................................................... 604/117
(58) Field of Classification Search
USPC .................... 604/117, 115, 263–264, 164.08
See application file for complete search history.

(56) References Cited

U.S. PATENT DOCUMENTS

| 5,312,335 | A | * | 5/1994 | McKinnon et al. | ............. 604/72 |
| 5,383,864 | A | * | 1/1995 | van den Heuvel | ............ 604/218 |
| 6,406,456 | B1 | * | 6/2002 | Slate et al. | ...................... 604/68 |
| 2001/0011171 | A1 | | 8/2001 | Alchas | |
| 2001/0012925 | A1 | | 8/2001 | Alchas | |
| 2001/0021832 | A1 | | 9/2001 | Numao et al. | |

(Continued)

FOREIGN PATENT DOCUMENTS

| JP | 57-45946 U | 9/1980 |
| JP | 1-82053 U | 6/1989 |

(Continued)

OTHER PUBLICATIONS

International Search Report (PCT/ISA/210) issued on Oct. 5, 2010, by Japanese Patent Office as the International Searching Authority for International Application No. PCT/JP2010/065247.

*Primary Examiner* — Nicholas Lucchesi
*Assistant Examiner* — Melissa A Snyder
(74) *Attorney, Agent, or Firm* — Buchanan Ingersoll & Rooney PC

(57) ABSTRACT

An injection aid is a tool used by being attached to an injection device having an injection needle and a syringe, and includes an aid main body and a tapered guide. The aid main body includes; an engagement part to be engaged with the syringe; a hollow part through which the injection needle penetrates; and a needle-protruding surface from which a needle tip part of the injection needle protrudes and which is brought into contact with skin when sticking the injection needle into a living body. The tapered guide is arranged in the hollow part of the aid main body and includes an inner surface that becomes continuously reduced in diameter toward the needle-protruding surface.

3 Claims, 7 Drawing Sheets

(56) References Cited

U.S. PATENT DOCUMENTS

| | | |
|---|---|---|
| 2001/0056263 A1 | 12/2001 | Alchas et al. |
| 2002/0038111 A1 | 3/2002 | Alchas et al. |
| 2002/0045858 A1 | 4/2002 | Alchas et al. |
| 2004/0220524 A1* | 11/2004 | Sadowski et al. ............. 604/117 |
| 2007/0118077 A1* | 5/2007 | Clarke et al. .................. 604/117 |
| 2008/0033395 A1 | 2/2008 | Alchas |
| 2008/0200881 A1* | 8/2008 | Emmott et al. ............... 604/192 |

FOREIGN PATENT DOCUMENTS

| | | |
|---|---|---|
| JP | 2000-37456 A | 2/2000 |
| JP | 2001-137343 A | 5/2001 |
| JP | 2001-190654 A | 7/2001 |

* cited by examiner

INJECTION AID AND MEDICATION SYRINGE DEVICE

TECHNICAL FIELD

The present invention relates to an injection aid and a medication syringe device (drug injection device) that are used to inject a drug into a skin upper layer part by sticking a needle tip from the skin surface into the skin upper layer part.

BACKGROUND ART

Recently, it has been reported that by administering flu vaccine targeting at an upper layer part of skin where many immunocompetent cells are present, even if the dosage is reduced, the same immunity acquisition ability as in subcutaneous administration or intramuscular administration can be obtained. Thus, by administering flu vaccine to the skin upper layer part, it is possible to reduce the dosage, so that there is a possibility that flu vaccine can be administered to more people. Note that the skin upper layer part refers to the epidermis and dermis of skin.

As the method of administering a drug to the skin upper layer part, methods using a single-needle, a multi-needle, a patch, gas, etc. are known. And, if stability and reliability of administration and production cost are considered, the method using a single needle is regarded most suitable for the method of administering a drug to the skin upper layer part. As the method of administering vaccine to the skin upper layer part using a single needle, a Mantoux method has been known from a long time ago. The Mantoux method is a method in which a needle, having generally 26-27 gauge in size and having a short bevel needle tip, is inserted into skin about 2-5 mm, from an oblique direction of about 10-15° relative to the skin, to administer a drug of about 100 μL.

However, the Mantoux method is difficult in manipulation, and the rate of success is left in the skill of the doctor giving an injection. In particular, a child has a possibility of moving at the time of administration, so that it is difficult to administer flu vaccine with the Mantoux method. Accordingly, it is desired that a device is developed that can administer vaccine to the skin upper layer part in a simple and convenient manner.

Patent Document 1 describes an injection device in which a limiter having a skin-contacting surface is connected with a needle hub mounted on a syringe. The limiter of the injection device described in Patent Document 1 is formed in a tube-like shape surrounding a needle tube, and has the skin-contacting surface from which an injection needle protrudes. The limiter regulates the length (protrusion length) of the injection needle protruding from the skin-contacting surface to 0.5-3.0 mm, and is adapted so that the drug injected from the injection needle is administered in the skin.

Patent Document 2 describes technique relating to a sticking adjustment tool for an injection needle that prevents an injection needle from being stuck deeper than a target depth and an injection needle assembly having the sticking adjustment tool. Sticking adjustment tools for an injection needle disclosed in Patent Document 2 include the one that is closely attached around an injection needle and has a skin-contacting surface.

Sometimes an injection device is used with suctioning a drug from a vial. The vial is a drug storage container capable of storing a drug for long periods in a liquid or freeze-dried state. The opening of the vial is sealed with a rubber stopper generally having the thickness of about 3-5 mm. The rubber stopper is made so as not to leak the drug even if the needle tube is stuck a plurality of times. Therefore, the majority of vaccine that is often vaccinated in a group setting is used by being suctioned from the vial.

The limiter described in Patent Document 1 and the sticking adjustment tool for an injection needle described in Patent Document 2 are configured to make the protrusion length of an injection needle relatively short (for example, 0.5-3.0 mm) so that the drug can be administered to the skin upper layer part. Therefore, it has led to that the injection needle cannot penetrate through the rubber stopper of a vial, and it has been impossible to suction the drug from the vial.

For example, if it is before the limiter described in Patent Document 1 is attached to the needle hub of an injection device, it is possible to suction the drug from a vial with the injection device. Also, if it is before the sticking adjustment tool for an injection needle described in Patent Document 2 is attached to an injection device, it is possible to suction the drug from a vial with the injection device.

Patent Document 1: Japanese Unexamined Patent Application Publication No. 2001-137343
Patent Document 2: Japanese Unexamined Patent Application Publication No. 2000-37456

DISCLOSURE OF THE INVENTION

Problems to be Solved by the Invention

However, when attaching the limiter described in Patent Document 1 to an injection device after suctioning the drug from a vial, attachment of the limiter to the injection device is carried out by the user. At this time, it is difficult to insert the injection needle of the injection device through the opening of the limiter, and the attachment work is troublesome. When attachment of the sticking adjustment tool for an injection needle described in Patent Document 2 to an injection needle is carried out by the user also, it is difficult to insert the injection needle through the hole ($25a$) of the sticking adjustment tool for an injection needle ($22a$), and the attachment work is troublesome.

Further, in these cases, it is conceivable that the needle tip is bent by touching walls of the limiter or the sticking adjustment tool for an injection needle when attaching. Also, when the limiter, etc. are formed of plastics, it is conceivable that the limiter, etc. are stuck by the needle tip.

The present invention has been made in view of the above-described circumstance, and aims to enable an injection aid to be easily and reliably attached to an injection device, the injection aid regulating the length of the part of an injection needle protruding from a needle-protruding surface at the needle tip side of the injection needle of the injection device.

Means for Solving the Problems

An injection aid according to the present invention is used by being attached to an injection device having an injection needle and a syringe, and includes an aid main body and a tapered guide. The aid main body includes an engagement part to be engaged with the syringe, a hollow part through which the injection needle penetrates, and a needle-protruding surface from which the needle tip part of the injection needle protrudes and which is brought into contact with skin when sticking the injection needle into a living body. The tapered guide is arranged in the hollow part of the aid main body, and includes an inner surface that becomes continuously reduced in diameter toward the needle-protruding surface.

A drug injection device of the present invention includes an injection device having an injection needle and a syringe, and an injection aid having an aid main body and a tapered guide. The aid main body of the injection aid includes an engagement part to be engaged with the syringe, a hollow part through which the injection needle penetrates, and a needle-protruding surface from which the needle tip part of the injection needle protrudes and which is brought into contact with skin when sticking the injection needle into a living body. The tapered guide is arranged in the hollow part of the aid main body, and includes an inner surface that becomes continuously reduced in diameter toward the needle-protruding surface.

When attaching the injection aid of the present invention to an injection device, the injection needle of the injection device is caused to penetrate through the tapered guide and thereby the injection needle penetrates through the hollow part of the aid main body. Since the inner surface of the tapered guide becomes continuously reduced in diameter toward the needle-protruding surface, it is possible to simply insert the injection needle into the tapered guide and reliably guide the needle tip toward the needle-protruding surface to protrude from the needle-protruding surface. As a result, the user can attach the injection aid to the injection device easily.

Effects of the Invention

According to the injection aid and the drug injection device of the present invention, it is possible to attach the injection aid to an injection device easily and reliably.

BEST MODE FOR CARRYING OUT THE INVENTION

Below, description will be made, referring to drawings, with respect to embodiments of an injection aid and a drug injection device of the present invention. Note that the common parts in respective drawings are denoted by the same references numerals.

1. First Embodiment

Injection Aid

First, description will be made with respect to the first embodiment of an injection aid of the present invention, referring to FIG. 1 through FIG. 4.

Figure 1:
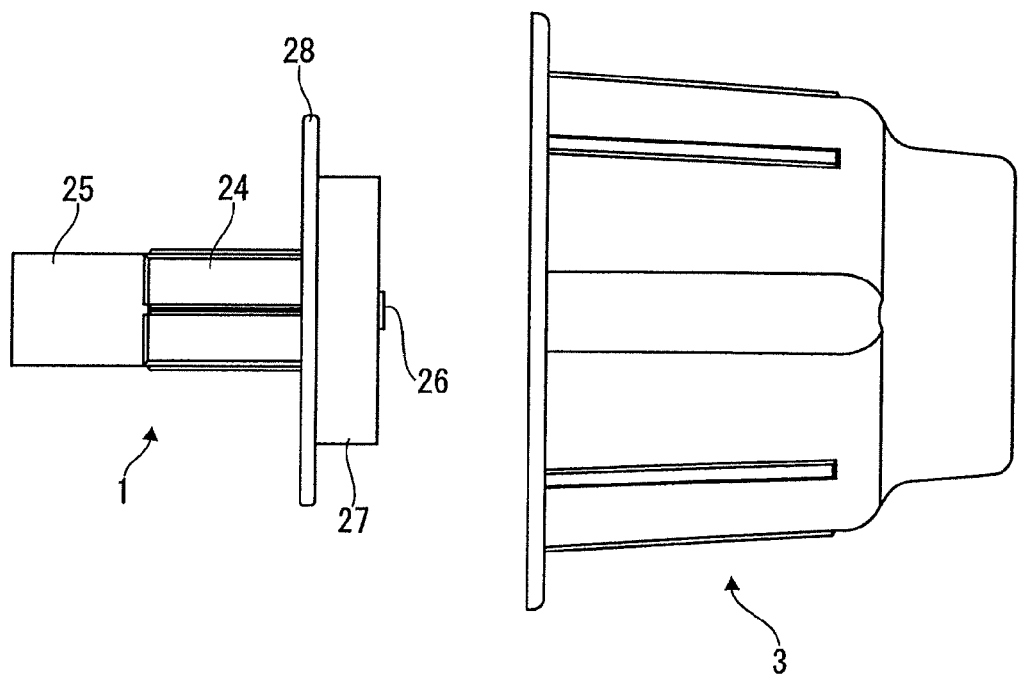
FIG. 1 is a side view illustrating the first embodiment of an injection aid of the present invention and a cap.
Figure 2:
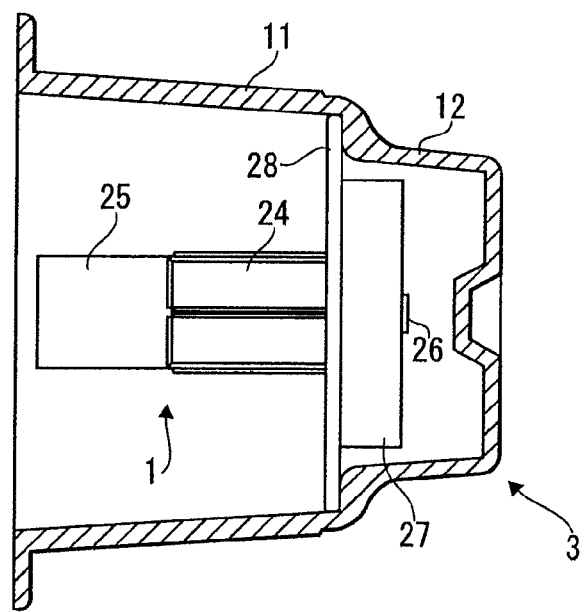
FIG. 2 is a partial cross-sectional view illustrating the first embodiment of the injection aid of the present invention and the cap.
Figure 3:
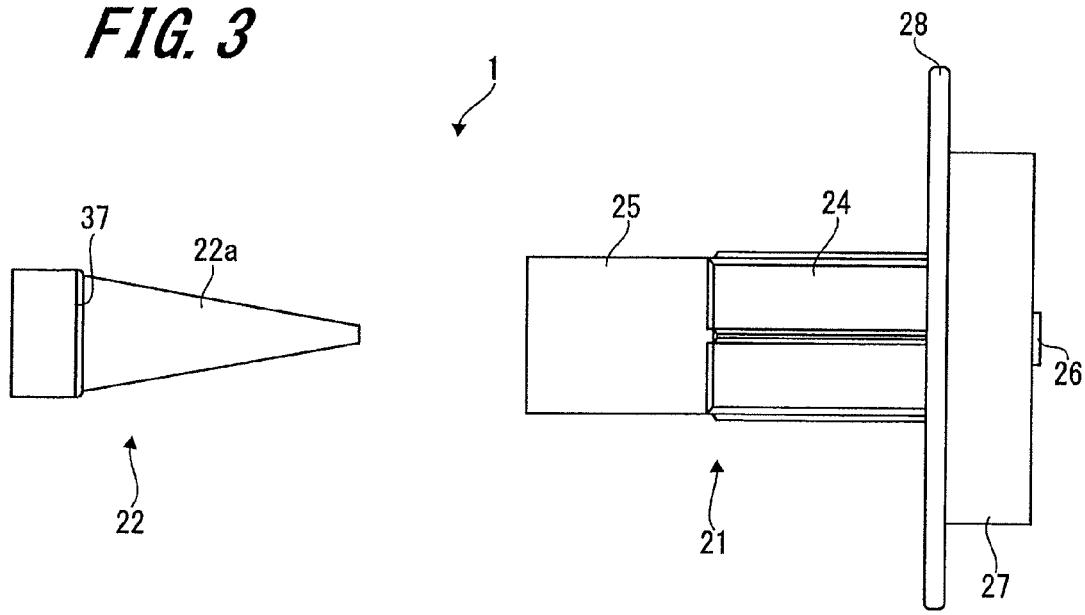
FIG. 3 is an exploded view illustrating the first embodiment of the injection aid of the present invention.
Figure 4:
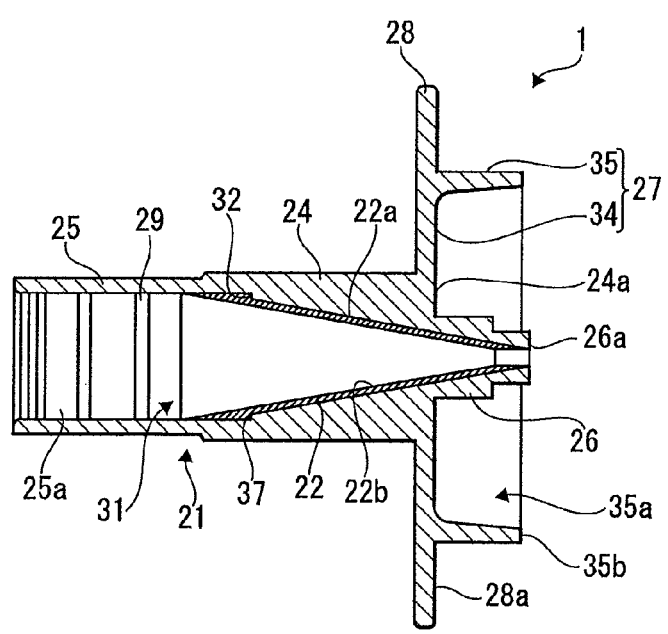
FIG. 4 is a cross-sectional view illustrating the first embodiment of the injection aid of the present invention.

FIG. 1 is a side view illustrating the first embodiment of an injection aid, and a cap. FIG. 2 is a partial cross-sectional view illustrating the first embodiment of an injection aid, and a cap. FIG. 3 is an exploded view of an injection aid. FIG. 4 is a cross-sectional view of an injection aid.

An injection aid 1 is used by being attached to an injection device 52 (see FIG. 5) when injecting a drug into the skin upper layer part by sticking the needle tip of an injection needle from the skin surface into the skin upper part. The injection aid 1 may have a cap 3 which is detachably attached.

As illustrated in FIG. 2, the cap 3 is formed in a tube-like shape with a closed end, and has flexibility. The cap 3 includes an engaging part 11 which engages with a later-described flange part 28 of the injection aid 1, and a needle-covering part 12 which is smaller in diameter than the engaging part 11. In a state that the injection aid 1 has been attached to the injection device 52, a needle tip part 53a of an injection needle 53 described later is arranged in the needle-covering part 12 (see FIG. 6).

The cap 3 has an open end, and by covering the end face of the open end with a sealing member (not shown), the cap 3 can be constituted to serve as a storage container of the injection aid 1. The cap 3 has also the function to serve as a holding part when attaching the injection aid 1 to the injection device 52. As the material for the cap 3, synthetic resin may be cited, such as polycarbonate, polypropylene, polyethylene, etc.

The injection aid 1 includes an aid main body 21, and a tapered guide 22 which is arranged in the aid main body 21. The aid main body 21 includes a base part 24, an engagement part 25, an adjustment part 26, a stabilization part 27, and a flange part 28. The base part 24 is formed in a tube-like shape. The engagement part 25 is formed at one end in the axial direction of the base part 24, and the adjustment part 26 is formed at the other end.

The engagement part 25 is formed in a cylindrical shape. The axial center of the engagement part 25 coincides with the axial center of the base part 24. The outer diameter of the engagement part 25 is approximately equal to the outer diameter of the base part 24. A later-described syringe 54 of the injection device 52 is engaged with the engagement part 25 by insertion. A plurality of projection parts 29 are formed in an inner surface 25a of the engagement part 25, each continuously projecting in a circumferential direction of the inner surface 25a. The projection parts 29 are brought into contact with the outer circumferential surface of the syringe 54.

The adjustment part 26 is provided in the center part of an end face 24a of the base part 24, and includes a cylindrical convex part protruding in an axial direction of the base part 24. The axial center of the adjustment part 26 coincides with the axial center of the base part 24. A hollow part 31 that communicates with the cylindrical hole of the engagement part 25 and that is opened at an end face of the adjustment part 26 is provided inside the base part 24 and the adjustment part 26.

The hollow part 31 decreases in size toward the end face of the adjustment part 26 from one end of the base part 24. As illustrated in FIG. 4, the tapered guide 22 is arranged in the hollow part 31, and the injection needle 53 of the injection device 52 penetrates through the tapered guide 22 (see FIG. 6). A locking part 32 with which a later-described step part 37 of the tapered guide 22 is brought in contact is provided in the inner surface of the base part 24 forming the hollow part 31.

Figure 6:
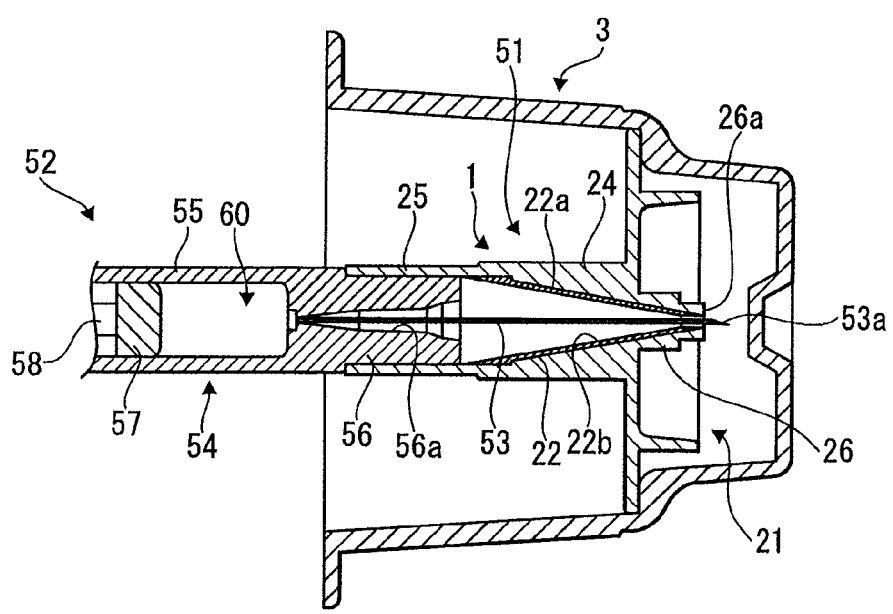
FIG. 6 is a cross-sectional view illustrating an embodiment of a drug injection device of the present invention after having been assembled.

The end face of the adjustment part 26 is formed to serve as a needle-protruding surface 26a from which the needle tip part 53a of the injection needle 53 protrudes (see FIG. 6). The needle-protruding surface 26a is formed as a flat surface that is perpendicular to the axial direction of the adjustment part 26. The needle-protruding surface 26a contacts the skin surface when sticking the injection needle 53 to the skin upper layer part and defines the depth to which the injection needle 53 is stuck into the skin upper layer part. That is, the depth to which the injection needle 53 is stuck into the skin upper layer part is determined by the length of the part of the injection needle 53 protruding from the needle-protruding surface 26a (herein below, referred to as "protrusion length L"). Description will be made later in detail with respect to the protrusion length L.

The stabilization part 27 includes a ring piece 34 protruding from the outer circumferential surface of the base part 24 in a radial direction of the base part 24, and a contact piece 35 continuing from the ring piece 34 and protruding in the axial direction of the base part 24. The contact piece 35 is formed in a shape of a cylinder having a cylindrical hole 35a, and the adjustment part 26 is arranged in the cylindrical hole 35a. That is, the stabilization part 27 surrounds the adjustment part 26.

An end face 35b of the contact piece 35 is a flat surface that is approximately parallel to the needle-protruding surface 26a of the adjustment part 26. The end face 35b contacts the skin surface when sticking the needle tip part 53a of the injection needle 53 protruding from the needle-protruding surface 26a into a living body. Note that the shape of the contact piece 35 is not limited to a circular cylindrical shape, and may be a rectangular cylindrical shape, such as a quadrangular column, a hexagonal column, etc., each having a cylindrical hole in the center.

The flange part 28 is provided on substantially the same plane as the ring piece 34, and is formed in a ring-like shape protruding from the outer circumferential surface of the contact piece 35 in a radial direction of the contact piece 35. The flange part 28 includes a contact surface 28a that contacts the skin surface when sticking the needle tip part 53a of the injection needle 53 protruding from the needle-protruding surface 26a to a living body. The contact surface 28a is a flat plane that is approximately parallel to the end face 35b of the stabilization part 27. The cap 3 is detachably fitted on the flange part 28.

The tapered guide 22 is formed of a material having a hardness equivalent to or higher than that of the injection needle 53, such as SUS 304, titanium, ceramic, etc., in a substantially conical tube-like shape. The step part 37 that is brought in contact with the locking part 32 of the aid main body 21 is provided on an outer surface 22a of the tapered guide 22. The step part 37 abuts on the locking part 32 of the aid main body 21, and thereby the tapered guide 22 is positioned relative to the aid main body 21. And, the tapered guide 22 is firmly fixed to the aid main body 21 by an adhesive agent (not shown) that is applied between the outer surface 22a of the tapered guide 22 and the inner surface of the aid main body 21 forming the hollow part 31.

An inner surface 22b of the tapered guide 22 forms a cylindrical hole in a shape of a circle, and the diameter of the cylindrical hole continuously decreases in size from the end part on the engagement part 25 side toward the end part on the needle-protruding surface 26a side. A coating agent (not shown), such as silicone resin, fluorocarbon resin, etc., is applied on the inner surface 22b of the tapered guide 22.

The coating agent is preferably applied so as to block an opening at the tip end side of the tapered guide 22. Thereby, the coating agent is surely applied to the needle tip part 53a of the injection needle 53 that has penetrated through the tapered guide 22. The roughness degree of the needle tip part 53a is smoothed by the coating agent applied on the surface of the needle tip part 53a. Thereby, the friction that is caused between the skin and the needle tip part 53a of the injection needle 53 can be reduced, easing the pain that will accompany when sticking the injection needle 53 to the skin, and enabling stable sticking of the injection needle 53 to the skin as well.

[Drug Injection Device]

Next, description will be made referring to FIG. 5 and FIG. 6, with respect to a drug injection device 51 of the present invention.

Figure 5:
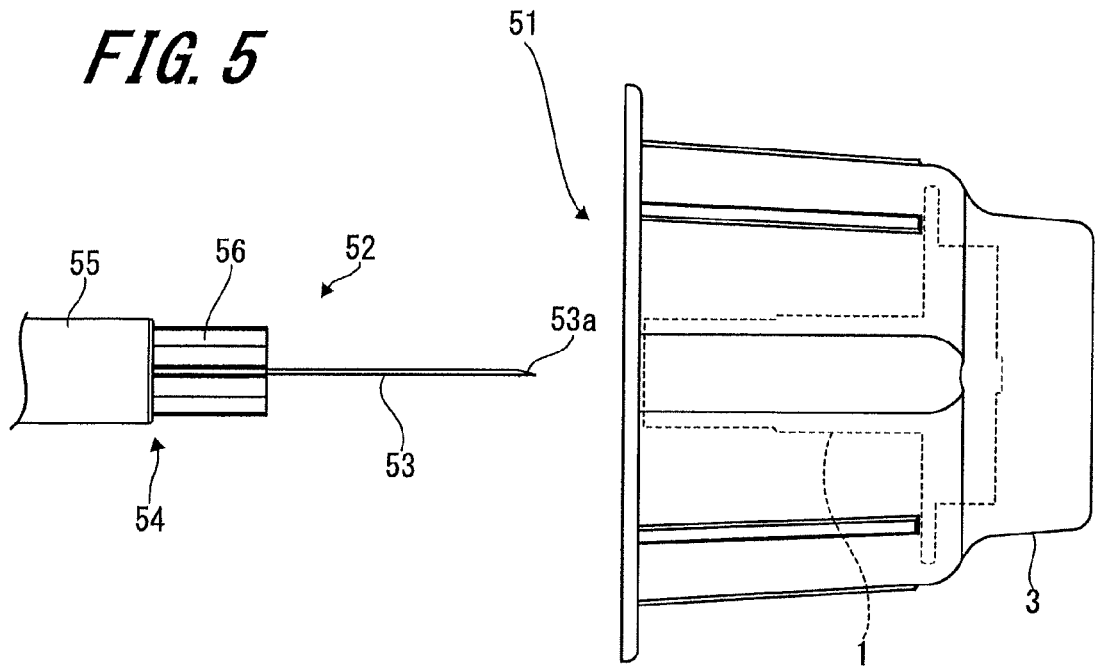
FIG. 5 is a side view illustrating an embodiment of a drug injection device of the present invention in a state immediately before it is assembled.

FIG. 5 is a side view illustrating the drug injection device 51 immediately before it is assembled. FIG. 6 is a cross-sectional view illustrating the drug injection device 51 after having been assembled.

The drug injection device 51 includes the injection device 52, and the injection aid 1 which will be attached to the injection device 52. The injection device 52 includes the injection needle 53 that is hollow, and a syringe 54 to which the injection needle 53 is attached.

For the injection needle 53, an injection needle with the size of 26-33 gauge (outer diameter; 0.2-0.45 mm) by ISO standards for medical needle tubes (ISO9626: 1991/Amd. 1:2001 (E)) is used. Preferably, an injection needle with the size of 30-33 gauge is used.

At one end of the injection needle 53, the needle tip part 53a, which has a blade face, is provided. As for the length of the blade face in the axial direction of the injection needle 53 (herein below, referred to as "bevel length B", see FIG. 7), it is all right if it is 1.4 mm, which is the thinnest thickness of the skin upper layer part (for adults) later described, or below. Also, it is all right if the bevel length B is about 0.5 mm or above, which is the bevel length when a short bevel is formed in a needle tube of 33 gauge. That is, it is preferable that the bevel length B is set in the range of 0.5-1.4 mm.

The bevel length B is more preferably 0.9 mm, which the thinnest thickness of the skin upper layer part (for children), or below. That is, the bevel length B is more preferably in the range of 0.5-0.9 mm. Note that the short bevel refers to a blade face forming at an angle of 18-25° relative to the longitudinal direction of a needle, which is generally used in injection needles.

As the material for the injection needle 53, for example, stainless steel may be cited. However, the material is not limited to this, and aluminum, aluminum alloy, titanium, titanium alloy, and other metals may be used. And, for the injection needle 53, not only a straight needle but also a tapered needle in which at least a part thereof is tapered may be used. The tapered needle may be configured, for example, such that the base end part has a larger diameter compared with the needle tip part and the intermediary part is tapered. Also, the cross-sectional shape of the injection needle 53 may be not only a circular shape but also a polygonal shape such as a triangular shape, etc.

The syringe 54 includes a tubular main body 55, and a needle hub 56 that continues from the tip of the tubular main body 55. The tubular main body 55 includes a circular cylindrical body. The needle hub 56 includes a circular cylindrical body having the outer diameter smaller than that of the tubular main body 55. The needle hub 56 is detachably inserted into the engagement part 25 of the injection aid 1.

As illustrated in FIG. 6, in the needle hub 56, a needle insertion part 56a, into which the base end side of the injection needle 53 is inserted, is provided. The injection needle 53 inserted into the needle insertion part 56a communicates with the inside of the tubular main body 55. The injection needle 53 is firmly fixed to the needle hub 56 by an adhesive agent (not shown) injected into the needle insertion part 56a.

Note that the needle hub 56 according to the present embodiment is formed such that a gap will not be caused between the injection needle 53 and the tubular main body 55, and therefore the drug is hard to remain in the syringe 54. Because the drug is hard to remain in the syringe 54, the merit of decreasing the antigen level that can be obtained by administering a vaccine to the skin upper layer part will not be damaged.

A gasket 57 is housed in the tubular main body 55. The space in the tubular main body 55 is partitioned by the gasket 57, and one space communicating with the injection needle 53 forms a liquid room 60. A plunger 58 is arranged in the other space of the tubular main body 55. One end (tip part) of the plunger 58 is connected with the gasket 57, and the other end (base end part) of the plunger 58 protrudes from an opening (not shown) of the tubular main body 55. By operating the plunger 58, the gasket 57 is moved in the axial direction in the tubular main body 55, and thereby suctioning of the drug to the liquid room 60 and discharging of the drug filled in the liquid room 60 are performed.

For the material of the syringe 54, synthetic resin (plastics) may be used, such as polycarbonate, polypropylene, polyethylene, etc., and also, metals, such as stainless steel, aluminum, etc. may be used.

[Assembly Method of a Drug Injection Device]

Next, description is made with respect to an assembly method of the drug injection device 51. As illustrated in FIG. 6, the drug injection device 51 is assembled by attaching the injection aid 1 to the injection device 52. For attaching the injection aid 1 to the injection device 52, first, the injection needle 53 is inserted from the side of the engagement part 25 of the injection aid 1, and the needle hub 56 is fitted into the engagement part 25. The insertion of the needle hub 56 is stopped by contact of the engagement part 25 with the tubular main body 55. Thereby, the needle tip part 53a of the injection needle 53 protrudes from the needle-protruding surface 26a provided in the adjustment part 26 of the injection aid 1, and assembly of the drug injection device 51 is completed.

At this time, the injection needle 53 passed through the engagement part 25 is moved through the tapered guide 22. Therefore, even if the axial center of the injection needle 53 and the center of the opening of the adjustment part 26 do not coincide with each other, the injection needle 53 is guided by the inner surface 22b of the tapered guide 22, and is moved toward the opening of the adjustment part 26. Accordingly, the injection needle 53 can reliably penetrate through the injection aid 1 until the needle tip part 53a protrudes from the opening of the adjustment part 26, and the injection aid 1 can be easily attached to the injection device 52.

Also, the coating agent applied on the inner surface 22b of the tapered guide 22 adheres to the needle tip part 53a of the injection needle 53 protruding from the needle-protruding surface 26a. Accordingly, even if a coating agent previously applied on the needle tip part 53a is peeled off when the injection needle 53 penetrates through a rubber stopper of a vial for obtaining a drug, it is possible to apply a coating agent again to the needle tip part 53a. As a result, the friction that will be caused between skin and the injection needle 53 can be reduced, easing the pain that will accompany when sticking the injection needle 53 to the skin, and enabling stable sticking of the injection needle 53 to the skin as well.

Further, the cap 3 is attached to the injection aid 1. Therefore, it is possible to prevent the needle tip part 53a of the injection needle 53 protruding from the needle-protruding surface 26a from touching a finger tip, etc. of the user. Note that when sticking the injection needle 53 to the skin upper lay part using the drug injection device 51, the cap 3 is detached from the injection aid 1.

[Protrusion Length]

Next, description will be made referring to FIG. 7, with respect to the protrusion length L which is the length of the part of the injection needle 53 protruding from the needle-protruding surface 26a.

Figure 7:
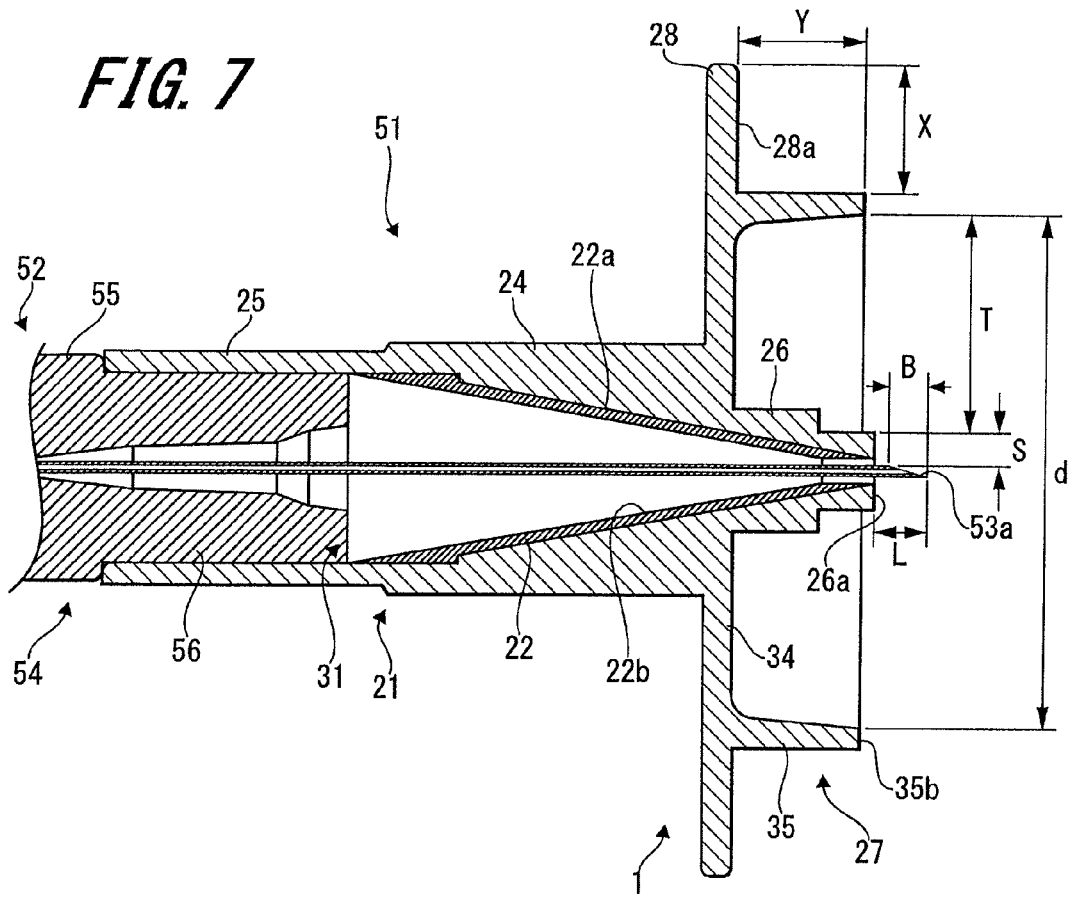
FIG. 7 is a cross-sectional view illustrating an embodiment of a drug injection device of the present invention in a state that a cap has been detached.

FIG. 7 is a cross-sectional diagram of the drug injection device 5 in a state that the cap 3 has been detached from the injection aid 1.

The thickness of the skin upper layer part corresponds to the depth of the epidermis layer and dermis layer from the skin surface, which is generally in the range of about 0.5-3.0 mm. Therefore, various dimensions of the injection aid 1 are set such that the protrusion length L of the injection needle 53 is in the range of 0.5-3.0 mm.

Meanwhile, vaccine is generally administered to the brachial region, and when administering vaccine to the skin upper layer part, it is preferable to administer vaccine to the periphery of the shoulder where the skin is relatively thick, in particular, to the deltoid muscle part. So, the thickness of the skin upper layer part of the deltoid muscle was measured with respect to 19 children and 31 adults. The measurement was carried out, using an ultrasonic measurement device (NP60R-UBM high-resolution echo for small animals, NEPA GENE, CO., LTD.), by imaging the skin tissue that has relatively high ultrasonic reflectivity. Here, because the measured values showed log-normal distribution, the range of MEAN±2SD was obtained by geometrical mean.

As a result, the thickness of the skin upper layer part of the deltoid muscle of children was 0.9-1.6 mm. The thickness of the skin upper layer part of the deltoid muscle of adults was 1.4-2.6 mm in the distal part, 1.4-2.5 mm in the middle part, and 1.5-2.5 mm in the proximal part. From the above, the thickness of the skin upper layer part of the deltoid muscle was confirmed as 0.9 mm or above in the case of children, and 1.4 mm or above in the case of adults. Consequently, in the injection into the skin upper layer part of the deltoid muscle, it is preferable to set the protrusion length L of the injection needle 53 in the range of 0.9-1.4 mm.

By setting the protrusion length L of the injection needle 53 in this manner, it becomes possible to securely position the blade face of the needle tip part 53a in the skin upper layer part. As a result, the needle hole (drug discharging outlet) opened in the blade face can be positioned in the skin upper layer part, regardless of where it is located in the blade face. Note that even when the drug discharging outlet is located in the skin upper layer part, if the needle tip part 53a is stuck deeper than the skin upper layer part, the drug escapes to the subcutaneous tissue from between the side face of the needle tip part 53a and the incision surface of the incised skin, so that it is important that the blade face is located in the skin upper layer part with certainty.

Note that in the case of a needle tube larger than 26 gauge, it is difficult to make the bevel length B 1.0 mm or below. Accordingly, to set the protrusion length L of the injection needle 53 in the preferable range (0.9-1.4 mm), it is desirable to use a needle tube that is smaller than 26 gauge.

The needle-protruding surface 26a is formed such that a distance S from the rim thereof to the outer circumferential surface of the injection needle 53 is 1.4 mm or below, preferably in the range of 0.3-1.4 mm. This distance S from the rim of the needle-protruding surface 26a to the outer circumferential surface of the injection needle 53 is set considering that pressure is given to a blister which is formed in the skin upper layer part by administering a drug to the skin upper layer part. That is, the needle-protruding surface 26a is configured to be sufficiently smaller than a blister to be formed in the skin upper layer part, in a size that will not block formation of a blister. Thereby, even if the needle-protruding surface 26a depresses the skin around the injection needle 53, formation of a blister will not be blocked, so that it can be prevented that the administered drug leaks to the outside of the skin.

[Dimensions of a Stabilization Part and a Flange Part]

Next, description will be made referring to FIG. 7, with respect to dimensions of the stabilization part 27 and the flange part 28.

The end face 35b of the stabilization part 27 is located slightly on the side of the base part 24 from the needle-protruding surface 26a of the adjustment part 26. Therefore, if the needle tip part 53a of the injection needle 53 is stuck into a living body, first, the needle-protruding surface 26a contacts the skin surface, and thereafter, the end face 35b of the stabilization part 27 contacts the skin surface. At this time, the drug injection device 51 is stabilized by the contact of the end face 35b of the stabilization part 27 with the skin, and the injection needle 53 can be held in a substantially perpendicular posture to the skin.

The injection needle 53 can be held in a substantially perpendicular posture to the skin even if the end face 35b of the stabilization part 27 is located on substantially the same plane as the needle-protruding surface 26a or located on the side of the needle tip part 53a of the injection needle 53 more than the needle-protruding surface 26a. Note that if a bulge of the skin, which is caused when the stabilization part 27 is pressed against the skin, is considered, it is preferable to set the distance in the axial direction between the end face 35b of the stabilization part 27 and the needle-protruding surface 26a to 1.3 mm or below.

The inner diameter d of the stabilization part 27 is set at a value equivalent to or larger than the diameter of a blister which is formed in the skin when a drug is administered to the skin upper layer part. Specifically, the inner diameter d is set such that a distance T from an internal wall surface of the stabilization part 27 to the rim of the needle-protruding surface 26a is in the range of 4-15 mm. Thereby, it is prevented that pressure is applied to a blister from the internal wall surface of the stabilization part 27 to disturb formation of the blister.

There is no upper limit particularly for the distance T from the internal wall surface of the stabilization part 27 to the rim of the needle-protruding surface 26a so long as it is 4 mm or above. However, if the distance T is increased, the outer diameter of the stabilization part 27 increases, so that when sticking the injection needle 53 to a thin arm like that of a child, it becomes difficult to cause the entire part of the end face 35b of the stabilization part 27 to contact the skin. Accordingly, considering the thinness of children's arms, it is preferable to specify the distance T to 15 mm at the maximum.

If the distance S from the rim of the needle-protruding surface 26a to the outer circumferential surface of the injection needle 53 is 0.3 mm or above, it will never occur that the adjustment part 26 penetrates the skin. Accordingly, if the distance T (4 mm or above) from the internal wall surface of the stabilization part 27 to the rim of the needle-protruding surface 26a and the diameter (about 0.3 mm) of the needle-protruding surface 26a are considered, the internal diameter d of the stabilization part 27 can be set to 9 mm or above.

When sticking the injection needle 53 into a living body, the stabilization part 27 is pressed to skin until the contact surface 28a of the flange part 28 contacts the skin. Thereby, it can be ensured that the force to press the stabilization part 27 and the injection needle 53 to the skin is always at a predetermined value or above. As a result, the part of the injection needle 53 protruding from the needle-protruding surface 26a (corresponding to the protrusion length L) is stuck into the skin upper layer part with certainty.

A distance (hereinafter referred to as "flange part height") Y from the contact surface 28a of the flange part 28 to the end face 35b of the stabilization part 27 is set in length such that the injection needle 53 and the stabilization part 27 are pressed to the skin with an appropriate pressing force and thereby the part of the injection needle 53 protruding from the needle-protruding surface 26a can be stuck into the skin. Thus, by pressing the injection needle 53 and the stabilization part 27 to the skin until the contact surface 28a of the flange part 28 contacts the skin, it is brought that the pressing force to press the injection needle 53 and the stabilization part 27 to the skin is at a predetermined value or above, and thereby the needle tip part 53a (blade face) of the injection needle 53 can be positioned in the skin upper layer part with certainty, and a sense of ease can be given to the user. Note that the appropriate pressing force to press the injection needle 53 and the stabilization part 27 to the skin is, for example, 3-20 N.

The flange part height Y is appropriately determined when the internal diameter d of the stabilization part 27 is within the range of 11-14 mm, based on a length X from the tip face of the flange part 28 to the outer circumferential surface of the stabilization part 27 (hereinafter referred to as "flange part length") For example, when the internal diameter d of the stabilization part 27 is 12 mm and the flange part length X is 3.0 mm, the flange part height Y is set in the range of 2.3-6.6 mm.

[Method of Using a Drug Injection Device]

Next, description will be made with respect to a method of using the drug injection device 51. To stick the needle tip part 53a of the injection needle 53 to a living body, first, the end face 35b of the stabilization part 27 is caused to face the skin. Thereby, the needle tip part 53a of the injection needle 53 faces the skin to be stuck. Next, the drug injection device 51 is moved substantially perpendicularly to the skin, the needle tip part 53a is stuck into the skin, and the end face 35b of the stabilization part 27 is pressed to the skin. At this time, the needle-protruding surface 26a contacts the skin. Therefore, the skin can be deformed so as to be flat, and the needle tip part 53a side of the injection needle 53 can be stuck into the skin by the protrusion length L.

Next, the end face 35b of the stabilization part 27 is pressed to skin until the contact surface 28a of the flange part 28 contacts the skin. Here, the flange part height Y is set in length such that the injection needle 53 and the stabilization part 27 are pressed to skin with an appropriate pressing force and the part of the injection needle 53 protruding from the needle-protruding surface 26a is stuck into the skin. Therefore, the force with which the skin is pressed by the stabilization part 27 becomes a predetermined value.

Accordingly, it is possible to cause the user to recognize the appropriate pressing force of the stabilization part 27 to the skin, and the needle tip part 53a and the blade face of the injection needle 53 can be surely positioned in the skin upper layer part. Thus, since the flange part 28 serves as a mark to recognize the appropriate pressing force by the injection needle 53 and the stabilization part 27 to the skin, the user can use the drug injection device 51 without fear.

Also, by causing the end face 35b of the stabilization part 27 to contact the skin, the posture of the drug injection device 51 is stabilized, and the injection needle 53 can be stuck straight to the skin. Furthermore, deviation that will be caused in the injection needle 53 after the injection needle 53 has been stuck to the skin can be prevented, and stable administration of the drug can be carried out.

When the protrusion length L is very short, for example, about 0.5 mm, even if the needle tip part 53a is caused to contact the skin, there is a case that the needle tip part 53a is not stuck into the skin. However, if the stabilization part 27 is pressed to the skin and the skin is depressed in a perpendicular direction, the skin on the inner side of the stabilization part 27 is extended and put in a condition that a tensional force has been applied to the skin. Therefore, the skin becomes hard to flee from the needle tip part 53a of the injection needle 53. Accordingly, by providing the stabilization part 27, an effect can be obtained also that it becomes easier for the needle tip part 53a to be stuck into the skin.

After causing the needle tip part 53a side of the injection needle 53 to be stuck to the skin, the plunger 58 is pushed, and the gasket 57 is moved toward the needle hub 56 (see FIG. 6). Thereby, the drug filled in the liquid room 60 of the tubular main body 55 is pushed out of the liquid room 60, passes through the needle hole of the injection needle 53, and is injected to the skin upper layer part from the needle tip part 53a.

2. Second Embodiment

Injection Aid

Next, description will be made referring to FIG. 8, with respect to the second embodiment of an injection aid of the present invention.

Figure 8:
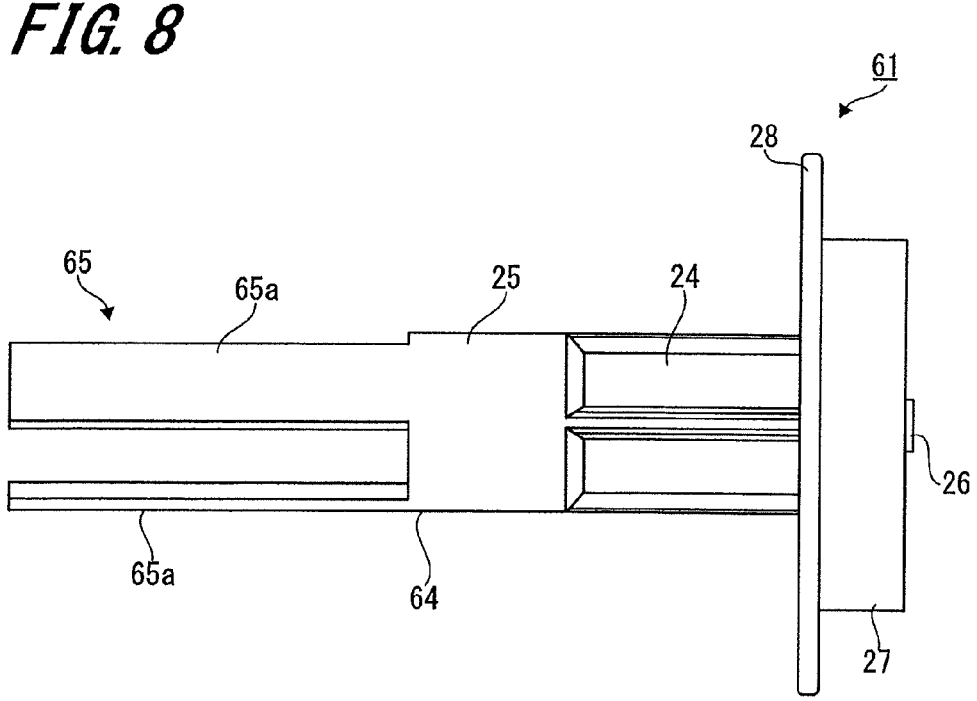
FIG. 8 is a side view illustrating the second embodiment of an injection aid of the present invention.

FIG. 8 is a side view of the second embodiment of an injection aid of the present invention.

An injection aid 61 has the constitution similar to that of the injection aid 1 according to the first embodiment. A difference of the injection aid 61 from the injection aid 1 is that an attachment guide part 65 is provided to an aid main body 64. Therefore, description will be made here with respect to the attachment guide part 65, and the common parts with the injection aid 1 are denoted by the same reference numerals and overlapped part of description is omitted.

The injection aid 61 includes the aid main body 64, and a tapered guide 22 (see FIG. 3) that is arranged in the aid main body 64.

The aid main body 64 includes a base part 24, an engagement part 25, an adjustment part 26, a stabilization part 27, a flange part 28, and the attachment guide part 65. The attachment guide part 65 is provided continuing from the end face of the engagement part 25. The attachment guide part 65 includes three arc-like guide pieces 65a arranged at appropriate intervals in the circumferential direction of the engagement part 25. Note that two guide pieces 65a are shown in FIG. 8.

The tubular main body 55 of the injection device 52 (see FIG. 5) is inserted into the attachment guide part 65. That is, the outer circumferential surface of the tubular main body 55 slidably contacts the inner surface of each guide piece 65a.

When the tubular main body 55 is inserted into the attachment guide part 65, the needle tip part 53a does not reach the tapered guide 22 which decreases in size of the diameter. Therefore, the injection needle 53 is positioned in a radial direction without touching the inner surface 22b of the tapered guide 22, and the axial center of the injection needle 53 coincides with the axial center of a hollow part 31 provided in the aid main body 64.

Figure 9A:
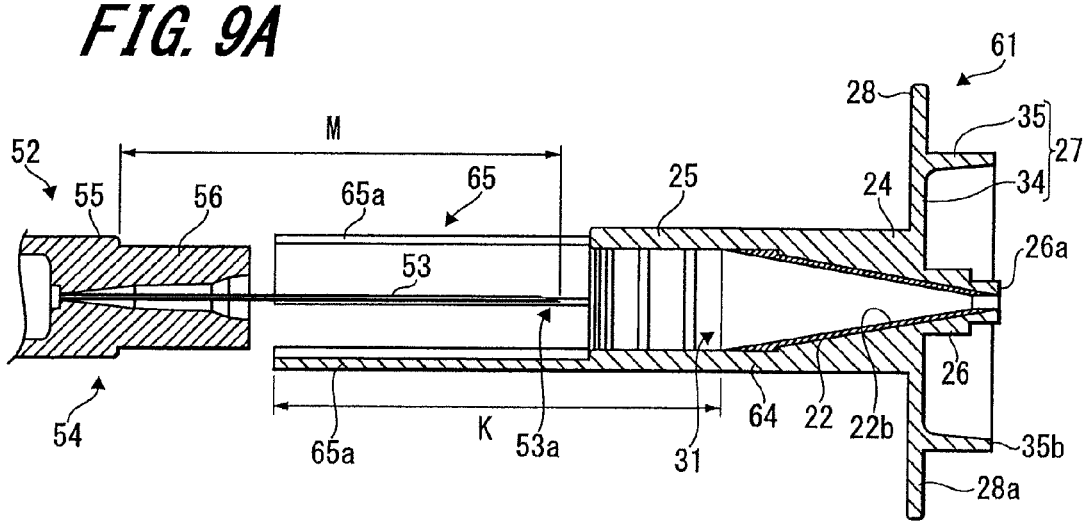
FIG. 9A, FIG. 9B, and FIG. 9C are explanatory diagrams respectively illustrating states of attaching the second embodiment of an injection aid of the present invention to an injection device.

A distance K from the tip end of each guide piece 65a to the end part on the engagement part 25 side of the tapered guide 22 is set equal to or longer than a distance M from the end face of the tubular main body 55 from which the needle hub 56 protrudes to the tip of the needle tip part 53a of the injection needle 53 (see FIG. 9A). Therefore, if the tubular main body 55 is inserted into the attachment guide part 65, the injection needle 53 is inserted into the tapered guide 22.

In the present embodiment, the attachment guide part 65 includes three guide pieces 65a and is configured such that the tubular main body 55 of the injection device 52 is slidably inserted. However, the number of the guide pieces according to the present invention may be two or less, or four or more.

[Method of Assembling a Drug Injection Device]

Next, description will be made with respect to a method of assembling a drug injection device 71, referring to FIG. 9A, FIG. 9B, and FIG. 9C.

FIG. 9A is an explanatory diagram of a state that the injection needle 53 of the injection device 52 has been caused to face the tapered guide 22 of the injection aid 61. FIG. 9B is an explanatory diagram of a state that the tubular main body 55 of the injection device 52 has been inserted into the attachment guide part 65 of the injection aid 61. FIG. 9C is an explanatory diagram of a state that attachment of the injection aid 61 to the injection device 52 has been completed.

The drug injection device 71 is assembled by attaching the injection aid 61 to the injection device 52. To attach the injection aid 61 to the injection device 52, first, the injection device 52 is displaced in a direction intersecting the axial direction, and the injection needle 53 is inserted through a gap between neighboring guide pieces 65a (see FIG. 9A). Thereby, the injection needle 53 can be easily caused to face the tapered guide 22.

Figure 9B:
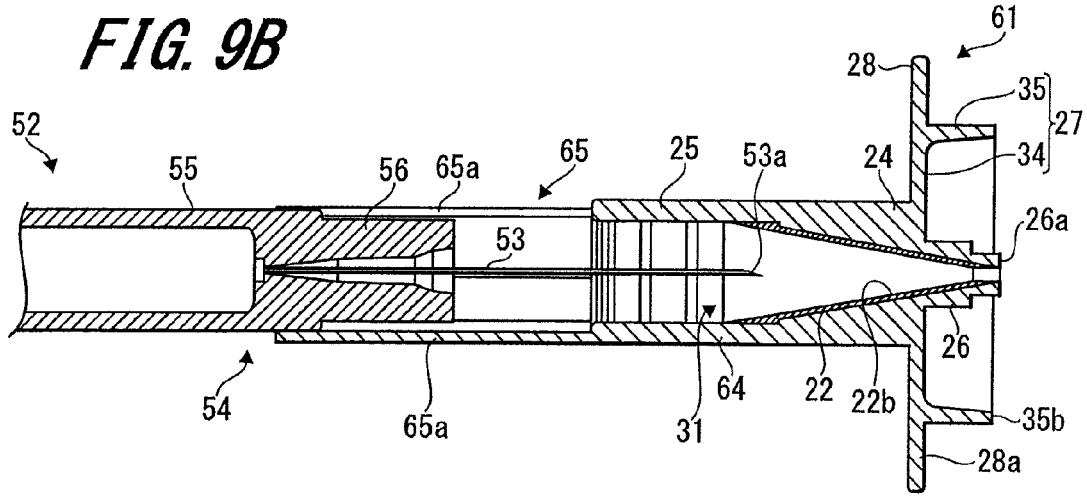
Figure 9C:
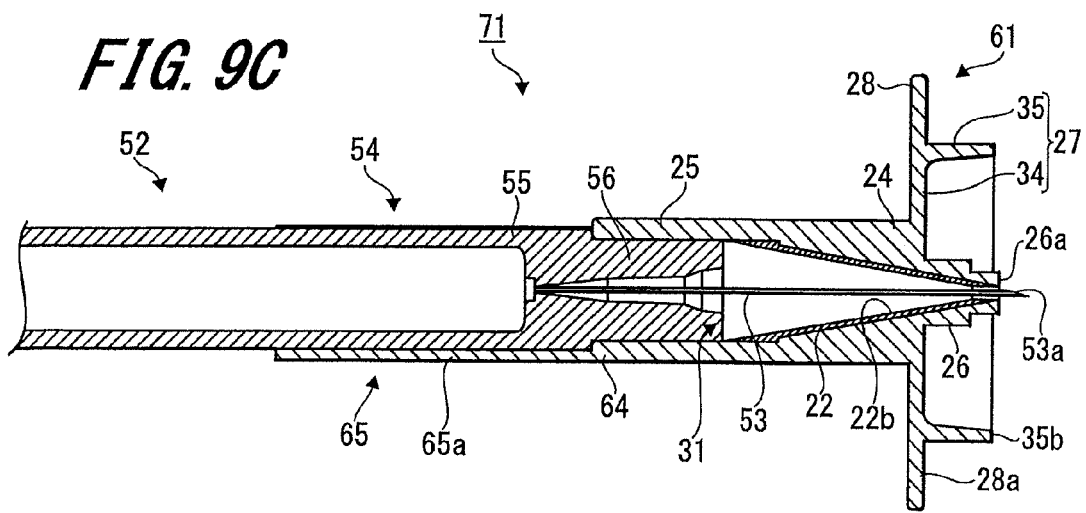

Next, the injection device 52 is moved in the axial direction, and the tubular main body 55 of the injection device 52 is inserted into the attachment guide part 65 (see FIG. 9B). At this time, the needle tip part 53a of the injection needle 53 begins to be inserted into the tapered guide 22, and the axial center of the injection needle 53 coincides with the axial center of the hollow part 31 and the tapered guide 22 of the injection aid 61.

Subsequently, the needle hub 56 of the injection device 52 is inserted into the engagement part 25 of the injection aid 61 (see FIG. 9C). Insertion of the needle hub 56 is stopped by contact of the engagement part 25 with the tubular main body 55, and the needle hub 56 is locked to the engagement part 25. Thereby, the needle tip part 53a of the injection needle 53 protrudes from the needle-protruding surface 26a provided in the adjustment part 26 of the injection aid 61, and assembling of the drug injection device 71 is completed.

At this time, because the axial center of the injection needle 53 coincides with the center of the opening (axial center of the hollow part 31) of the adjustment part 26, it is possible to cause the injection needle 53 to move toward the opening of the adjustment part 26. Further, even if bending deformation has been caused in the injection needle 53 when the injection needle 53 was caused to penetrate through the rubber stopper of a vial, the injection needle 53 is guided to the inner surface 22b of the tapered guide 22, so that the injection needle 53 advances toward the opening of the adjustment part 26. Accordingly, the needle tip part 53a of the injection needle 53 can certainly penetrate through the opening of the adjustment part 26, and the injection aid 61 can be easily attached to the injection device 52.

Further, in the drug injection device 71, scale marks provided in the tubular main body 55 of the injection device 52 can be visible through the gap of neighboring guide pieces 65a.

3. Third Embodiment

Injection Aid

Next, description will be made with respect to the third embodiment of an injection aid of the present invention, referring to FIG. 10.

Figure 10:
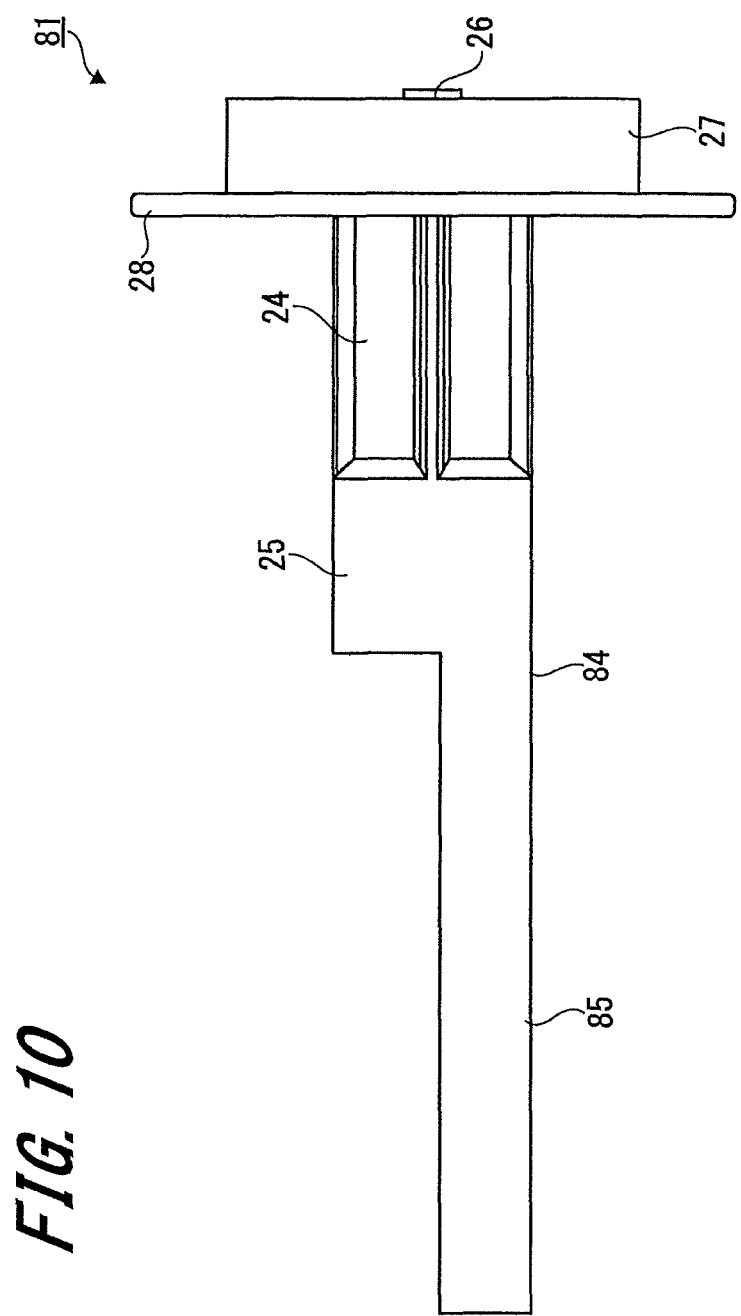
FIG. 10 is a side view illustrating the third embodiment of an injection aid of the present invention.

FIG. 10 is a side view of the third embodiment of an injection aid.

An injection aid 81 has the constitution similar to that of the injection aid 1 according to the first embodiment. A difference of the injection aid 81 from the injection aid 1 is that an attachment guide part 85 is provided to an aid main body 84. Therefore, description will be made here with respect to the attachment guide part 85, and the common parts with the injection aid 1 are denoted by the same reference numerals and overlapped part of description is omitted.

The injection aid 81 includes the aid main body 84, and a tapered guide 22 (see FIG. 3) arranged in the aid main body 84. The aid main body 84 includes a base part 24, an engagement part 25, an adjustment part 26, a stabilization part 27, a flange part 28, and the attachment guide part 85. The attachment guide part 85 is provided continuing from the end face of the engagement part 25. The attachment guide part 85 is formed in an arc-like shape with the center angle of 180 degrees, that is, in a shape of a cylinder cut in half.

Figure 11A:
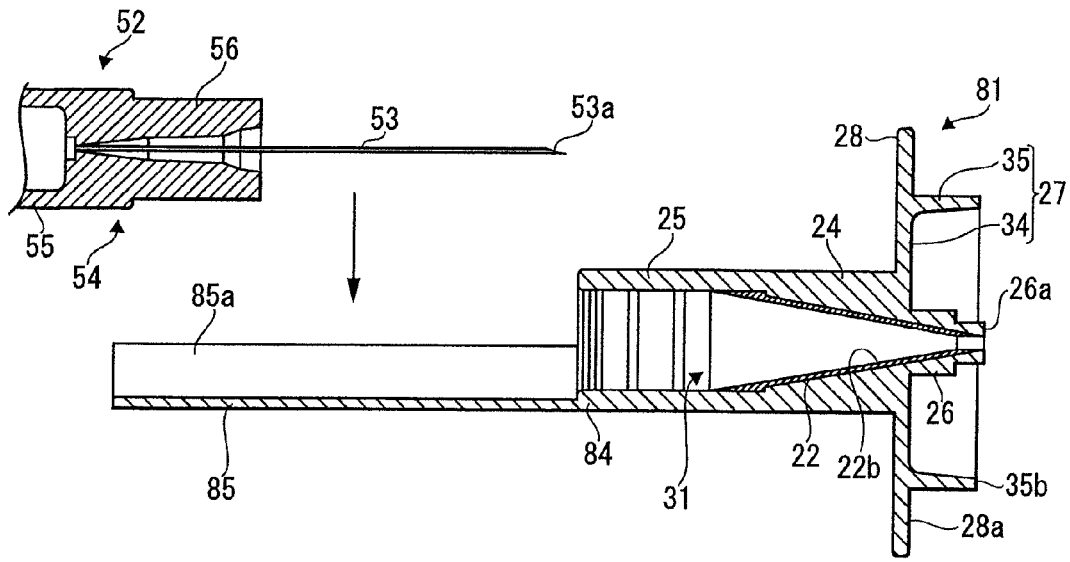
FIG. 11A, FIG. 11B, and FIG. 11C are explanatory diagrams respectively illustrating states of attaching the third embodiment of an injection aid of the present invention to an injection device.
Figure 11B:
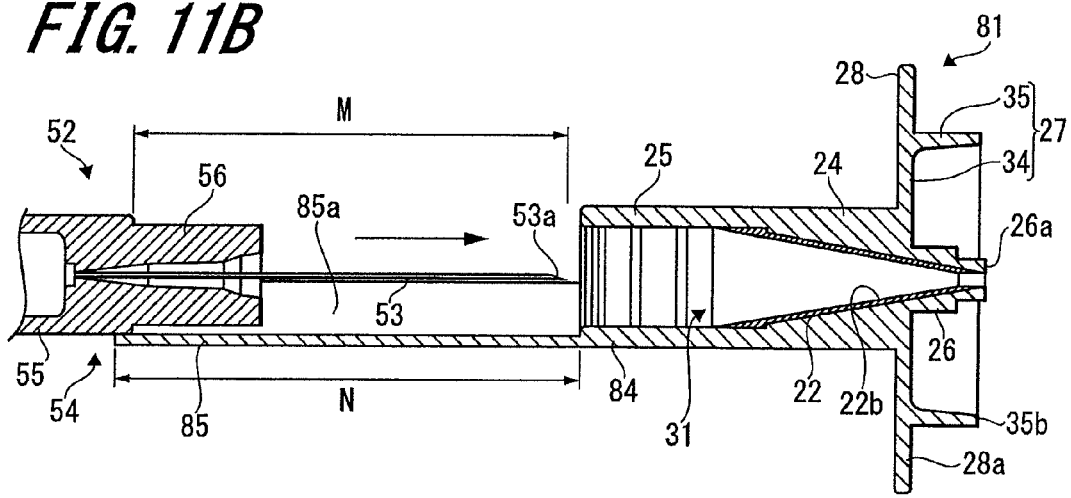
Figure 11C:
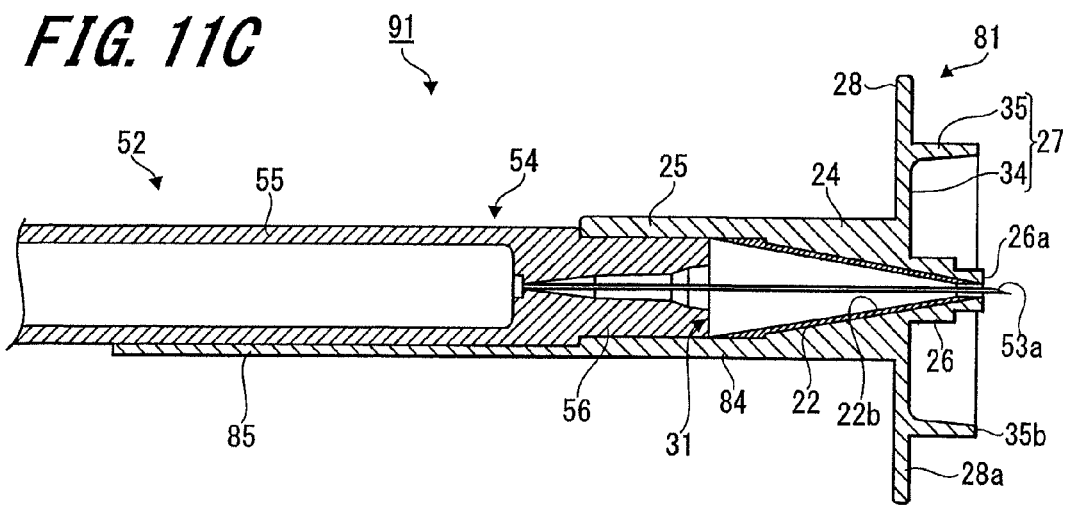

The outer circumferential surface of the tubular main body 55 of the injection device 52 (see FIG. 5) slidably contacts an inner surface 85a of the attachment guide part 85 (see FIGS. 11A-11C). It is configured such that when the outer circumferential surface of the tubular main body 55 contacts the inner surface 85a of the attachment guide part 85, the axial center of the injection needle 53 coincides with the axial center of a hollow part 31 provided in the aid main body 84.

A distance N from the tip of the attachment guide part 85 to the end face of the engagement part 25 is set longer than the length M from the end face of the tubular main body 55 from which the needle hub 56 protrudes to the tip of the needle tip part 53a of the injection needle 53 (see FIG. 11B). Therefore, by moving the injection device 52 in the direction intersecting the axial direction, the outer circumferential surface of the tubular main body 55 can be brought in contact with the inner surface 85a of the attachment guide part 85.

In the present embodiment, the attachment guide part 85 has been formed in an arc-like shape with the center angle of 180 degrees, however, the center angle of the attachment guide part according to the present invention may be smaller than 180 degrees. Further, the shape of the attachment guide part according to the present invention is not limited to an arc-like shape, and for example, may be a U-like shape in the cross section, wherein three side plates forming the U-like shape in the cross section respectively line contacting with the outer circumferential surface of the tubular main body 55.

[Method of Assembling a Drug Injection Device]

Next, description will be made with respect to a method of assembling the drug injection device 91, referring to FIG. 11A, FIG. 11B, and FIG. 11C.

FIG. 11A is an explanatory diagram of a state that the injection device 52 is moved in a direction intersecting the axial direction, close to the injection aid 81. FIG. 11B is an explanatory diagram of a state that the tubular main body 55 of the injection device 52 has been brought in contact with the internal surface 85a of the attachment guide part 85 of the injection aid 81. FIG. 11C is an explanatory diagram of a state that attachment of the injection aid 81 to the injection device 52 has been completed.

The drug injection device 91 is assembled by attaching the injection aid 81 to the injection device 52. To attach the injection aid 81 to the injection device 52, first the injection device 52 is displaced in a direction intersecting the axial direction, close to the attachment guide part 85 of the injection aid 81 (see FIG. 11A).

Thereby, the outer circumferential surface of the tubular main body 55 of the injection device 52 is brought in contact with the internal surface 85a of the attachment guide part 85, and the needle tip part 53a of the injection needle 53 faces the engagement part 25 (see FIG. 11B). At this time, the axial center of the injection needle 53 coincides with the axial center of the hollow part 31 and the tapered guide 22 of the injection aid 81. Further, because the attachment guide part 85 is formed in an arc-like shape with the center angel of 180 degrees, it is possible to prevent the injection device 52 from being displaced in a direction intersecting the axial direction.

Next, the injection device 52 is moved in the axial direction, and the needle hub 56 of the injection device 52 is inserted into the engagement part 25 (see FIG. 11C). Insertion of the needle hub 56 is stopped when the engagement part 25 abuts the tubular main body 55, and the needle hub 56 is locked to the engagement part 25. Thereby, the needle tip part 53a of the injection needle 53 protrudes from the needle-protruding surface 26a provided in the adjustment part 26 of the injection aid 81, and assembling of the drug injection device 91 is completed.

At this time, because the axial center of the injection needle 53 coincides with the center of the opening (axial center of the hollow part 31) of the adjustment part 26, it is possible to move the injection needle 53 toward the opening of the adjustment part 26. Further, even if bending deformation has been caused in the injection needle 53 when the injection needle 53 was caused to penetrate through the rubber stopper of a vial, the injection needle 53 is guided to the inner surface 22b of the tapered guide 22, so that the injection needle 53 is moved toward the opening of the adjustment part 26. Accordingly, it is possible to cause the needle tip part 53a of the injection needle 53 to certainly penetrate through the opening of the adjustment part 26, and the injection aid 81 can be easily attached to the injection device 52.

Furthermore, in the drug injection device 91, because the half in the circumferential direction of the outer circumferential surface of the tubular main body 55 is exposed, scale marks provided in the tubular main body 55 of the injection device 52 are visible.

So far, description has been made with respect to embodiments of an injection aid and a drug injection device of the present invention, including operations and effects thereof. However, the injection aid and the drug injection device of the present invention are not limited to the above-described embodiments, and various modified exploitations are possible within the scope not departing from the gist of the invention described in claims.

In the above-described embodiments, the engagement part 25 is formed in a tube-like shape, and the needle hub 56 is inserted therein. However, the engagement part according to the present invention is not limited to the tube-like shape, and can be appropriately changed depending on the shape and constitution of a syringe that will be attached.

In the above-described embodiments, the tapered guide 22 has been formed in a substantially conical tube-like shape. However, as the tapered guide according to the present invention, it will be sufficient so long as it has the internal surface continuously decreasing in diameter toward the end part on the needle-protruding surface side, and the outer shape may be appropriately formed according to the shape of the hollow part.

Further, in the above-described embodiments, the tapered guide 22 is formed such that one end thereof reaches the opening on the adjustment part 26 side of the aid main body. However, as the tapered guide according to the present invention, it is sufficient if the opening of the tapered guide at one end on the adjustment part 26 side is substantially equal in size to the opening on the adjustment part 26 side, and does not need to reach the opening on the adjustment part 26 side.

Furthermore, in the above-described embodiments, the cap 3 is formed so as to cover the base part 24, the engagement part 25, and the adjustment part 26 of the injection aid 1. However, as the cap according to the present invention, it is sufficient if it is formed to cover at least the adjustment part 26, and for example, it may be formed so as to fit into the contact piece 35 of the stabilization part 27.

EXPLANATION OF REFERENCE NUMERALS

1, 61, 81: injection aid, 3: cap, 21, 64, 84: aid main body, 22: tapered guide, 22a: outer surface, 22b: inner surface, 24: base part, 25: engagement part, 26: adjustment part, 26a: needle-protruding surface, 27: stabilization part, 28: flange part, 29: projection part, 31: hollow part, 32: locking part, 37: step part, 51, 71, 91: drug injection device, 52: injection device, 53: injection needle, 53a: needle tip part, 54: syringe, 55: tubular main body, 56: needle hub, 57: gasket, 58: plunger, 60: liquid room, 65, 85: attachment guide part, 65a: guide piece

The invention claimed is:

1. A drug injection device comprising:
  an injection device having an injection needle and a syringe; and
  an injection aid configured to be attached to the injection device, the injection aid including;
    an aid main body having an engagement part to be engaged with the syringe, a hollow part through which the injection needle penetrates, and a needle-protruding surface from which a needle tip part of the injection needle protrudes and which is brought into contact with skin when sticking the injection needle into a living body; and
    a tapered guide arranged in the hollow part of the aid main body, a distal portion of the tapered guide including an inner surface that becomes continuously reduced in diameter toward the needle-protruding surface.

2. The drug injection device according to claim 1, wherein said aid main body and said tapered guide are configured to obtain a predetermined protrusion length of the injection needle, the predetermined protrusion length defined by a length of the injection needle that protrudes from the needle-protruding surface.

3. The drug injection device according to claim 1, wherein the tapered guide is fixedly secured in the hollow part of the aid main body so as to define a predetermined protrusion length of the injection needle protruding past the needle-protruding surface.

* * * * *